United States Patent [19]

Stokker et al.

[11] 4,156,005

[45] May 22, 1979

[54] DERIVATIVES OF 1,2-BENZISOXAZOLES

[75] Inventors: Gerald E. Stokker, Gwynedd Valley; Edward J. Cragoe, Jr., Lansdale, both of Pa.

[73] Assignee: Merck & Co., Inc., Rahway, N.J.

[21] Appl. No.: 917,692

[22] Filed: Jun. 21, 1978

[51] Int. Cl.² .................. C07D 261/20; A61K 31/42
[52] U.S. Cl. ............................ 424/272; 260/307 DA; 260/566 A; 260/600 R
[58] Field of Search ................ 260/307 DA; 424/272

[56] References Cited

U.S. PATENT DOCUMENTS 3,794,734  2/1974  Cragoe et al. .................. 424/330

OTHER PUBLICATIONS

Kemp et al.—Tetrahedron 21, 3019–3021, (1965).
Lindemann et al.—C. A. 20, 403⁸, (1926).
Caronna et al.—C. A. 54, 22571i–22572a, (1960).
Saunders et al.—C. A. 83, 97263n, (1975).

*Primary Examiner*—Raymond V. Rush

*Attorney, Agent, or Firm*—Raymond M. Speer; Mario A. Monaco

[57] ABSTRACT

Substituted 1,2-benzisoxazoles of the formula

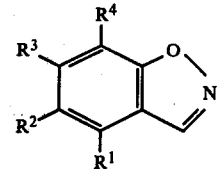

where:
 $R^1$ and $R^3$=H or lower alkoxy;
 $R^2$=halo or α-branched lower alkyl;
 $R^4$=halo, halo lower alkyl, or lower alkylthio; provided, where $R^1$ and $R^3$=H,
 $R^2$ and $R^4$ are other than simultaneously Cl or Br, which are active as antiinflammatory, antipyretic and analgesic agents, are derived from cyclodehydrating the corresponding salicylaldoximes with an isocyanate under extremely mild conditions.

8 Claims, No Drawings

4,156,005

DERIVATIVES OF 1,2-BENZISOXAZOLES

BACKGROUND OF THE INVENTION

This invention relates to a class of strategically substituted 1,2-benzisoxazoles with antiinflammatory, antipyretic and analgesic activity prepared from cyclodehydration of corresponding salicylaldoximes with an isocyanate under unexpectedly mild conditions.

Although the first 1,2-benzisoxazoles were prepared almost a century ago, they had not been made from salicylaldoximes employing an isocyanate as the cyclodehydration reagent until the present invention. In fact, according to K. H. Wünsch and A. J. Boulton in "Advances in Heterocyclic Chemistry," Vol. 8, Academic Press, New York and London, 1967, Pg. 283, "salicylaldoxime itself does not give 1,2-benzisoxazoles directly."

Since 1,2-benzisoxazoles are usually quite sensitive to both heat and base, and earlier syntheses generally required pyrolysis or alkaline decomposition, the scope of their derivatization, as well as the exploration of their pharmaceutical usages has been far from complete. It is with the newly discovered method of the present invention that many new derivatives of 1,2-benzisoxazole are made available for pharmaceutical studies including tests for antiinflammatory, antipyretic, and analgesic activities.

In recent years, non-steroidal antiinflammatory agents have been sought after to circumvent the undesirable side effects of steroidal agents. It is, therefore, an object of the present invention to provide new 1,2-benzisoxazoles of novel structures.

It is also an object of the present invention to provide a novel process for the preparation of these novel antiinflammatory, antipyretic and analgesic agents.

A further object of this invention is to provide a novel method of treating pain, fever and inflammation by administration of the novel compounds of this invention to a patient.

Finally an object of this invention is to provide novel pharmaceutical compositions comprising one or more of the novel compounds of this invention as active ingredient.

DETAILED DESCRIPTION OF THE INVENTION

The present invention concerns new 1,2-benzisoxazoles of formula:

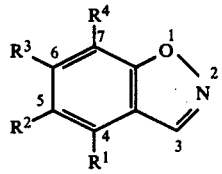

wherein:
$R^1$ and $R^3$ are independently hydrogen or lower alkoxy, especially $C_{1-4}$ alkoxy such as methoxy, ethoxy, propoxy, or butoxy;
$R^2$ is halo, such as iodo, bromo, chloro of fluoro, or α-branched lower alkyl, especially $C_{3-6}$ alkyl such as i-propyl, t-butyl, α,α-dimethylpropyl, or α-methylpentyl or the like;
$R^4$ is halo such as iodo, bromo, chloro or fluoro, halo lower alkyl, especially halo $C_{1-3}$ alkyl wherein the halo group is fluoro or chloro such as trifluoromethyl, fluoromethyl, trichloromethyl, α,α-difluoroethyl or perchloropropyl, lower alkylthio, especially lower $C_{1-3}$ alkylthio such as methylthio, ethylthio or propylthio, providing that wherein $R^1$ and $R^3$ are both hydrogen, $R^2$ and $R^4$ are other than simultaneously chlorine or bromine.

A preferred embodiment of this invention is that wherein:
$R^1$ and $R^3$ are independently hydrogen or $C_{1-3}$ alkoxy such as methoxy, ethoxy or propoxy;
$R^2$ is halo, or α-branched $C_{3-5}$ alkyl such as I-propyl, t-butyl, α-methylpropyl or α, α-dimethylpropyl; and
$R^4$ is halo, halo-$C_{1-3}$ alkyl, or $C_{1-3}$ alkylthio,
providing that wherein $R^1$ and $R^3$ are both hydrogen, $R^2$ and $R^4$ are other than simultaneously chlorine or bromine.

The more preferred embodiments of this invention are those:
(1) Wherein:
$R^1$ and $R^3$ are independently hydrogen or methoxy;
$R^2$ is α-branched $C_{3-5}$ alkyl; and
$R^4$ is iodo, halo-$C_{1-3}$ alkyl, $C_{1-3}$ alkylthio;
(2) Wherein:
$R^1$ and $R^3$ are independently $C_{1-3}$ alkoxy;
$R^2$ is halo; and
$R^4$ is halo.

The still more preferred embodiments of this invention are those:
(1) Wherein:
$R^1$ and $R^3$ are both hydrogen;
$R^2$ is α-branched $C_{3-5}$ alkyl; and
$R^4$ is iodo, fluoro-$C_{1-3}$ alkyl.
(2) Wherein:
$R^1$ and $R^3$ are both methoxy;
$R^2$ is halo; and
$R^4$ is halo.

The most preferred embodiments of this invention are three compounds:
(1) 5,7-dichloro-4,6-dimethoxy-1,2-benzisoxazole;
(2) 5-(1,1-dimethylethyl)-7-iodo-1,2-benzisoxazole;
(3) 5-(1,1-dimethylethyl)-7-trifluoromethyl-1,2-benzisoxazole.

The new 1,2-benzisoxazoles are prepared by a novel process comprising the treatment of a suitably substituted salicylaldoxime of formula:

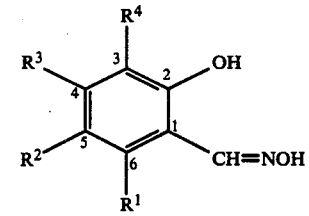

wherein $R_1$, $R_2$, $R_3$ and $R_4$ are as previously defined, with an isocyanate of formula:

R—N=C=O wherein R is $C_{1-3}$ alkylcarbonyl such as acetyl, methylacetyl or propionyl, perchloro or perfluoro $C_{1-3}$ alkylcarbonyl such as trichloroacetyl, trifluoroacetyl or perfluoropropionyl, phenyl or substituted phenyl such as p-chlorophenyl or α,α,α-trifluoro-o-tolyl or p-toluenesulfonyl, preferably trichloroacetyl or phenyl, in an inert solvent such as ether, for example, tetrahydrofuran, dioxane, 1,2-dimethoxyethane, diethylether, or an inert aromatic solvent including benzene, toluene, xylene or the like, preferably tetrahydrofuran, at about 10°-40° C., preferably 15°-25° C., until reaction is complete, usually about 10 minutes to about 16 hours, preferably 1.5 hours to 6 hours, followed by treatment with water or a weak base such as potassium carbonate, sodium bicarbonate, sodium carbonate, or ammonium hydroxide to afford a derivative of 1,2-benzisoxazole in about 40–97% yield.

The starting salicylaldoximes of the novel process are either known or prepared by a known process involving the treatment of a substituted 2-aminomethylphenol hydrochloride with hexamethylenetetramine in acetic acid followed by treatment with hydrochloric acid to give the corresponding salicylaldehyde followed by treatment with hydroxylamine hydrochloride.

A novel method of this invention comprises the administration of a 1,2-benzisoxazole, for example, 5,7-dichloro-4,6-dimethoxy-1,2-benzisoxazole, to a patient suffering pain, fever or inflammation. The route of administration can be oral, rectal, intraveneous, intramuscular, or intraperitoneal. Doses of 0.1 to 20 mg/kg/day and preferably of 0.5 to 10 mg/kg/day of an active ingredient are generally adequate, and it is preferred that it be administered in divided doses given two to four times daily.

It is to be noted that the precise unit dosage form and dosage level depend upon the case history of the individual being treated and, consequently, are left to the discretion of a skilled therapist.

Pharmaceutical compositions comprising a compound useful in the novel method of treatment as an active ingredient may be in any art recognized form suitable for oral use, such as tablets, troches, lozenges, aqueous or oil suspensions, disperisble powders or granules, emulsions, hard or soft capsules, syrups, or elixirs. For intravenous and intramuscular and intraperitoneal use, the pharmaceutical compositions may be in any art recognized form of a sterile injectable preparation such as sterile aqueous or oleaginous solution or suspension. The amount of the active ingredient incorporated in a unit dosage of the above described pharmaceutical composition may be from 1 to 400 mg, and preferably from 5 to 250 mg.

EXAMPLE 1

5-(1,1-Dimethylethyl)-7-iodo-1,2-benzisoxazole

Step A: Preparation of 5-(1,1-Dimethylethyl)-3-iodosalicylaldehyde

To a solution of 2-aminomethyl-4-(1,1-dimethylethyl)-6-iodophenol hydrochloride (51.3 g) in 1.4 l of 78.6% by volume aqueous acetic acid is added a solution of hexamethylenetetramine (22.05 g) in water (75 ml) providing a clear solution which is stirred and heated at reflux for 4 hours. The reaction mixture is treated with 4.5 N hydrochloric acid (225 ml) and heated at reflux for 15 minutes. Upon slowly cooling to −10° C., the 5-(1,1-dimethylethyl)-3-iodosalicylaldehyde is deposited as pale yellow crystals (20.4 g, 44.7%), m.p. 76°-78° C. Sublimation gives analytically pure 5-(1,1-dimethylethyl)-3-iodosalicylaldehyde, m.p. 77° C.

Step B: Preparation of 5-(1,1-dimethylethyl)-3-iodosalicylaldoxime

A solution of sodium acetate trihydrate (5.44 g) in water (10 ml) is added to a warm solution of 5-(1,1-dimethylethyl)-3-iodosalicylaldehyde (6 g) and hydroxylamine hydrochloride (3.5 g) in 80% by volume aqueous ethanol (50 ml). After refluxing for 3 hours the reaction mixture is diluted with hot water (10 ml) and then cooled to 0° C. to provide 5.5 g of 5-(1,1-dimethylethyl)-3-iodosalicylaldoxime, m.p. 154°–156° C.

Step C: Preparation of 5-(1,1-Dimethylethyl)-7-iodo-1,2-benzisoxazole

To a solution of 3.19 g of 5-(1,1-dimethylethyl)-3-iodosalicylaldoxime in 10 ml of tetrahydrofuran is added 2.0 g of trichloroacetylisocyanate in tetrahydrofuran (5 ml) at room temperature followed by addition of 1.52 g of potassium carbonate. The mixture is stirred for an additional 20 minutes before it is poured into 400 ml of water. The precipitate so obtained is crystallized from methanol to afford 1.4 g (46.5%) of 5-(1,1-dimethylethyl)-7-iodo-1,2-benzisoxazole, m.p. 106°–109° C.

Following essentially the same procedures of Steps A and B of Example 1, but replacing the 2-aminomethyl-4-(1,1-dimethylethyl)-6-iodophenol hydrochloride used therein with the appropriately substituted 2-aminomethylphenol hydrochlorides, as indicated in equation (a), a number of substituted salicylaldoximes are prepared as summarized in Table I.

TABLE I

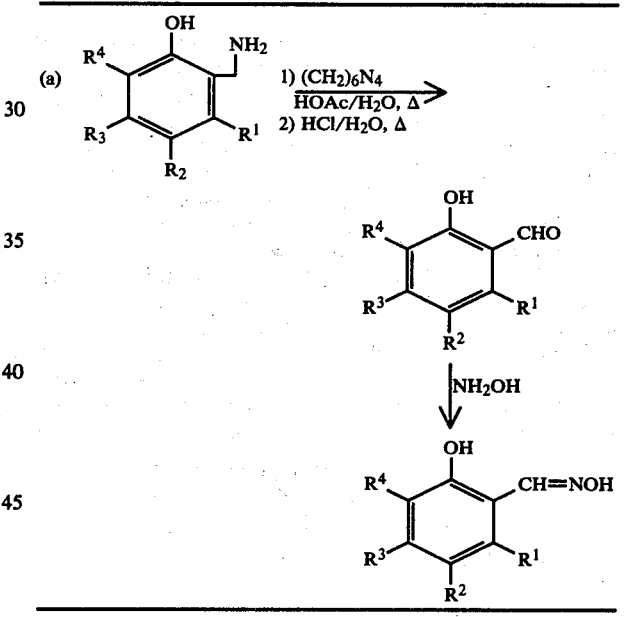

SUBSTITUTED SALICYLALDOXIMES

| Example | R¹ | R² | R³ | R⁴ | m.p. |
|---|---|---|---|---|---|
| 2 | H | t-C₄H₉ | H | Cl | 167°–169° C. |
| 3 | H | t-C₄H₉ | H | CH₃S | — |
| 4 | H | CH₃CH₂—C(CH₃)₂ | H | I | — |
| 5 | CH₃O | t-C₄H₉ | H | Cl | — |
| 6 | H | I | H | I | — |
| 7 | CH₃O | Cl | CH₃O | Br | — |
| 8 | H | i-C₃H₇ | H | Cl | — |
| 9 | H | t-C₄H₉ | H | CH₃CH₂S | — |
| 10 | C₂H₅O | Cl | C₂H₅O | Cl | — |

EXAMPLE 11

5,7-Dichloro-4,6-dimethoxy-1,2-benzisoxazole

Phenylisocyanate (1.19 g) is added slowly to a solution of 2.66 g of 3,5-dichloro-4,6,-dimethoxysalicylaldoxime in 20 ml of tetrahydrofuran. The clear solution is allowed to stand at room temperature for 16 hours. It is poured into 250 ml of water and the resulting precipitate is filtered, washed with water, and recrystallized from ethanol to give 1.4 g (56.5%) of 5,7-dichloro-4,6-dimethoxy-1,2-benzisoxazole, m.p. 138°–140° C.

EXAMPLE 12

4,6-Dimethoxy-1,2-benzisoxazole

Following the procedure substantially the same as described in Example 1, Step C, 1.97 g of 4,6-dimethoxysalicylaldoxime is treated with 2.0 g of trichloroacetylisocyanate to yield 1.3 g (72.6%) of 4,6-dimethoxy-1,2-benzisoxazole, m.p. 100°–101° C.

Employing substantially similar procedures described in Example 1, Step C, but substituting for the 5-(1,1-dimethylethyl)-3-iodosalicylaldoxime used therein similar stoichiometric amounts of the substituted salicylaldoximes previously described in Table I, there are produced, by the new process shown below in equation (b), a group of the corresponding 1,2-benzisoxazoles (1) wherein $R^1$, $R^2$, $R^3$ and $R^4$ are also defined by Table I.

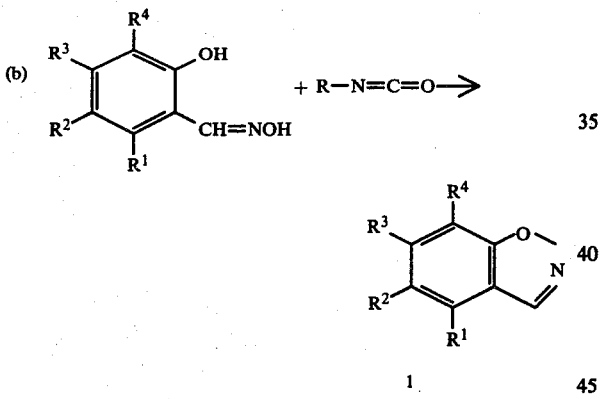

EXAMPLE 13

Pharmaceutical Compositions

A typical tablet containing 100 mg of 5,7-dichloro-4,6-dimethoxy-1,2-benzisoxazole is prepared by mixing together with the active ingredient calcium phosphate, lactose and starch in the amounts as shown below in Table II. After these ingredients are thoroughly mixed, the appropriate amount of magnesium stearate is added and the dry mixture is then compressed into tablets weighing approximately 223 mg each.

TABLE II

| Tablet Formula | |
| --- | --- |
| Ingredient | Mg per Tablet |
| 5,7-dichloro-4,6-dimethoxy-1,2-benzisoxazole | 100 |
| Calcium phosphate | 52 |
| Lactose | 60 |
| Starch | 10 |
| Magnesium stearate | 1 |

What is claimed is:

1. A compound of formula:

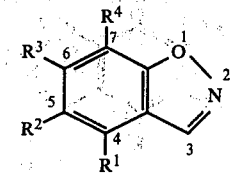

wherein:

$R^1$ and $R^3$ are independently hydrogen or lower alkoxy;

$R^2$ is halo or α-branched lower alkyl; and $R^4$ is halo, halo lower alkyl or lower alkylthio, providing that wherein $R^1$ and $R^3$ are both hydrogen, $R^2$ and $R^4$ are other than simultaneously chlorine or bromine.

2. The compound of claim 1 wherein:

$R^1$ and $R^3$ are independently $C_{1-3}$ alkoxy;

$R^2$ is halo; and $R^4$ is halo.

3. The compound of claim 1 wherein:

$R^1$ and $R^3$ are both hydrogen;

$R^2$ is α-branched $C_{3-5}$ alkyl; and $R^4$ is iodo or fluoro $C_{1-3}$ alkyl.

4. The compound of claim 1 selected from:

(1) 5,7-dichloro-4,6-dimethoxy-1,2-benzisoxazole;

(2) 5-(1,1-dimethylethyl)-7-iodo-1,2-benzisoxazole; and (3) 5-(1,1-dimethylethyl)-7-trifluoromethyl-1,2-benzisoxazole.

5. A method of treating pain, fever or inflammation which comprises the administration to a patient in need of such treatment an effective amount of a 1,2-benzisoxazole of formula:

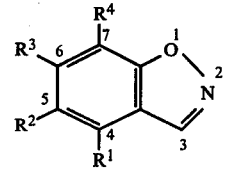

wherein:

$R^1$ and $R^3$ are independently hydrogen or lower alkoxy;

$R^2$ is halo or α-branched lower alkyl; and $R^4$ is halo, halo lower alkyl or lower alkylthio, providing that wherein $R^1$ and $R^3$ are both hydrogen, $R^2$ and $R^4$ are other than simultaneously chlorine or bromine.

6. The method of claim 5 wherein the 1,2-benzisoxazoles are selected from:

(1) 5,7-dichloro-4,6-dimethoxy-1,2-benzisoxazole;

(2) 5-(1,1-dimethylethyl)-7-iodo-1,2-benzisoxazole; and (3) 5-(1,1-dimethylethyl)-7-trifluoromethyl-1,2-benzisoxazole.

7. A pharmaceutical composition in unit dosage form for treating pain, fever or inflammation comprising a pharmaceutical carrier and a therapeutically effective amount of a 1,2-benzisoxazole of formula:

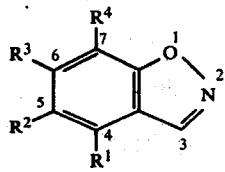

wherein:

R[1] and R[3] are independently hydrogen or lower alkoxy;

R[2] is halo or α-branched lower alkyl and

R[4] is halo, halo lower alkyl or lower alkylthio, providing that wherein R[1] and R[3] are both hydrogen, R[2] and R[4] are other than simultaneously chlorine or bromine.

8. The pharmaceutical composition of claim 7, in which the 1,2-benzisoxazoles are selected from:

(1) 5,7-dichloro-4,6-dimethoxy-1,2-benzisoxazole;

(2) 5-(1,1-dimethylethyl)-7-iodo-1,2-benzisoxazole; and (3) 5-(1,1-dimethylethyl-7-trifluoromethyl-1,2-benzisoxazole.

* * * * *